(12) United States Patent
Foreman et al.

(10) Patent No.: US 6,193,727 B1
(45) Date of Patent: Feb. 27, 2001

(54) SYSTEM FOR REMOVABLY SECURING A STENT ON A CATHETER ASSEMBLY AND METHOD OF USE

(75) Inventors: Philip C. Foreman, San Jose; Timothy A. Limon, Cupertino; Richard J. Saunders, Redwood City; Björn G. Svensson, Morgan Hill; Gregory W. Teaby, II, Sunnyvale, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/245,449

(22) Filed: Feb. 5, 1999

(51) Int. Cl.[7] ............................. A61F 02/02; A61M 29/00
(52) U.S. Cl. ............................................ 606/108; 606/198
(58) Field of Search ................................. 606/108, 191, 606/192, 194, 198; 604/96, 101

(56) References Cited

U.S. PATENT DOCUMENTS

| 4,733,665 | | 3/1988 | Palmaz . | |
|---|---|---|---|---|
| 5,078,720 | * | 1/1992 | Burton et al. | 606/108 |
| 5,360,401 | * | 11/1994 | Turnland | 604/96 |
| 5,507,768 | * | 4/1996 | Lau et al. | 606/198 |
| 5,653,691 | * | 8/1997 | Rupp et al. | 604/96 |
| 5,810,871 | * | 9/1998 | Tuckey et al. | 606/198 |
| 5,830,217 | * | 11/1998 | Ryan | 606/108 |
| 5,893,852 | * | 4/1999 | Morales | 606/108 |

\* cited by examiner

*Primary Examiner*—Paul J. Hirsch
*Assistant Examiner*—Michael B. Priddy
(74) *Attorney, Agent, or Firm*—Fulwider Patton Lee & Utecht, LLP

(57) ABSTRACT

A catheter system for removably securing a stent which generally includes an inner tubular member and an outer tubular member with an expandable member disposed about the inner tubular member. A deformable material is disposed between the expandable member and the inner tubular member. An expandable stent is crimped onto the expandable member and is retained in place by compressing the deformable material. Used with a stent delivery system, the catheter system is inserted into a body lumen such as an artery. The stent is secured in place while advancing the system through tortuous body lumen passages. The stent is advanced to the desired location in the body lumen and implanted by inflating the expandable member and thereby expanding the stent into the body lumen. The stent is released from the system by deflating the expandable member and withdrawing the catheter system from the body.

29 Claims, 5 Drawing Sheets

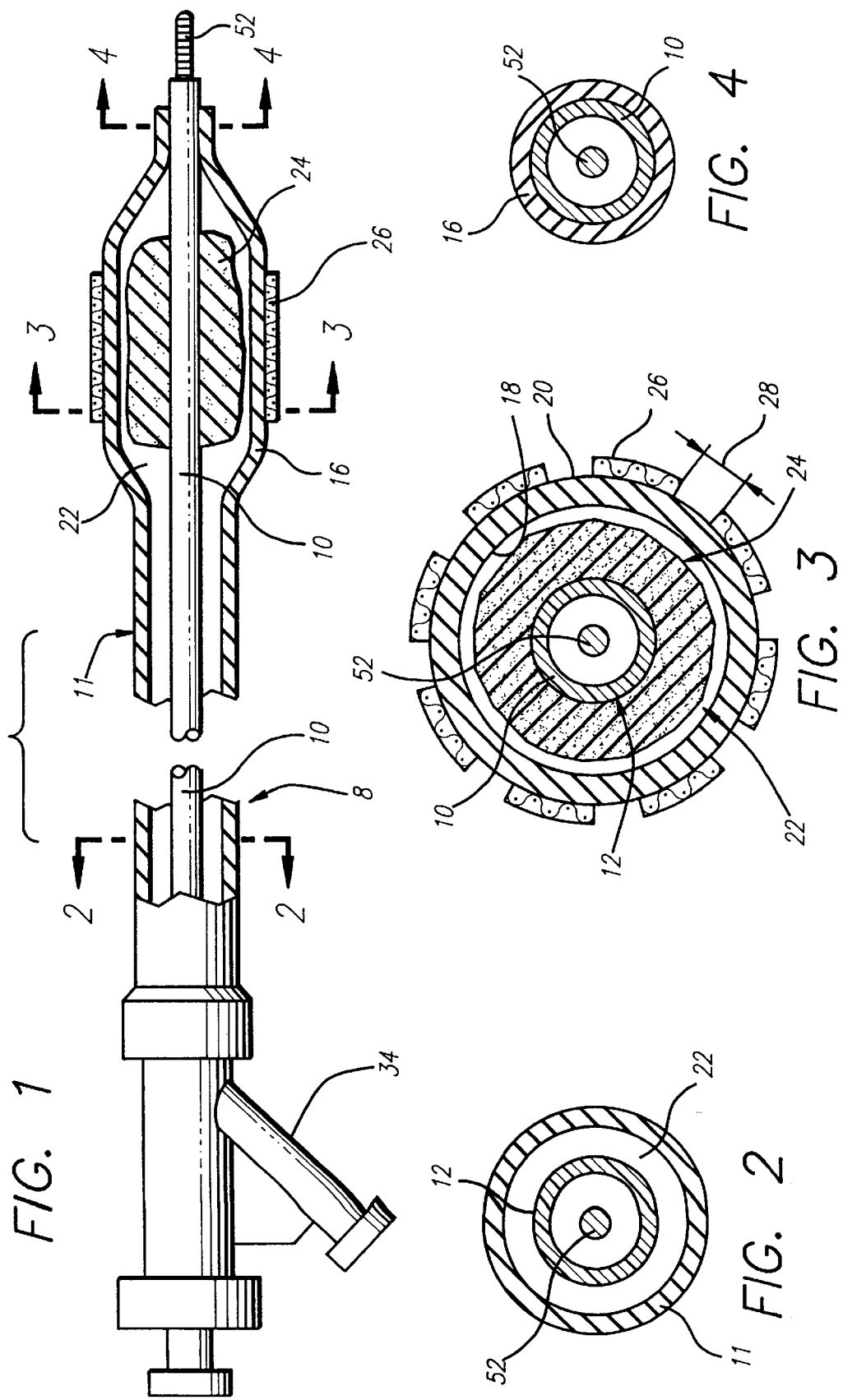

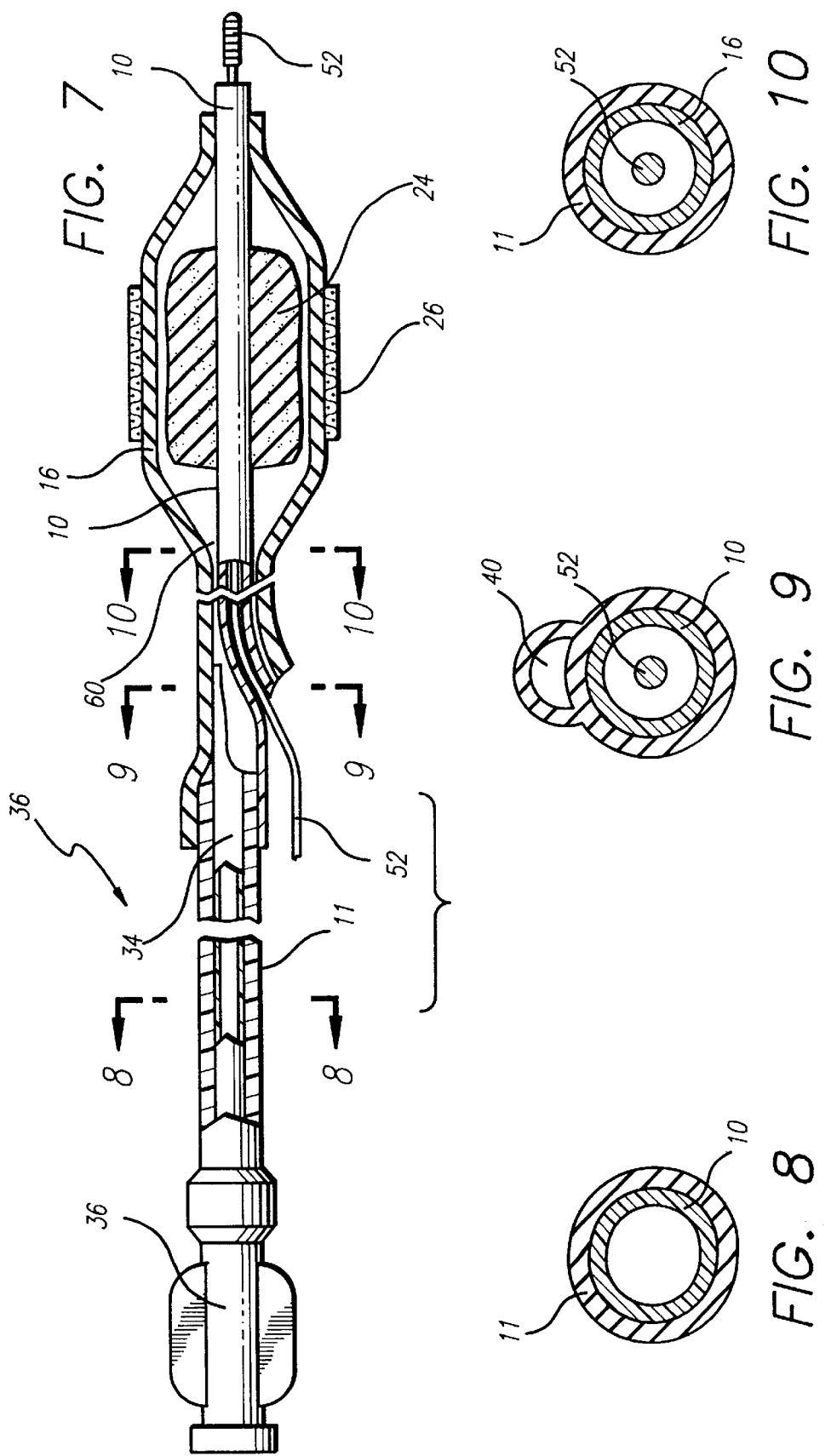

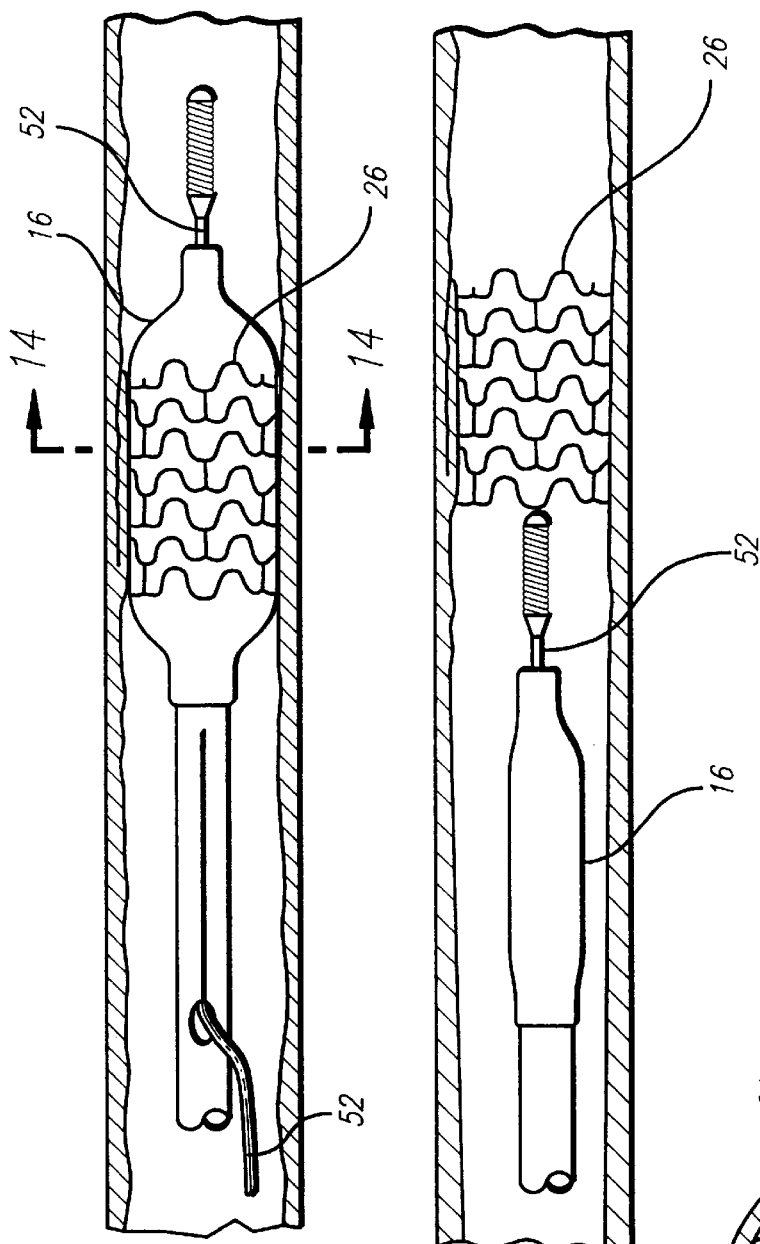
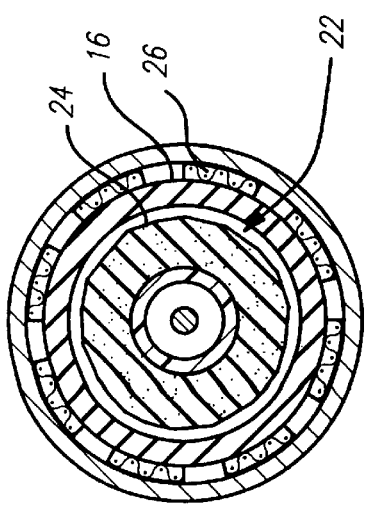
FIG. 13
FIG. 15
FIG. 14

SYSTEM FOR REMOVABLY SECURING A STENT ON A CATHETER ASSEMBLY AND METHOD OF USE

BACKGROUND OF THE INVENTION

This invention relates to devices for the treatment of heart disease and particularly to endo-arterial prosthesis, which are commonly called stents. More particularly, the invention relates to catheter assemblies for removably securing the stent to the catheter during delivery through a body lumen.

Several interventional treatment modalities are presently used for heart disease including balloon and laser angioplasty, atherectomy and by-pass surgery. In typical balloon angioplasty procedures, a guiding catheter having a preformed distal tip is percutaneously introduced through the femoral artery into the cardiovascular system of a patient in a conventional Seldinger technique and advanced within the cardiovascular system until the distal tip of the guiding catheter is seated in the ostium. A guidewire is positioned within an inner lumen of a dilatation catheter and then both are advanced through the guiding catheter to the distal end thereof The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the balloon, which is made of relatively inelastic materials, is inflated to a predetermined size with radiopaque liquid at relatively high pressure (e.g., greater than 4 atmospheres) to compress the arteriosclerotic plaque of the lesion against the inside of the artery wall and to otherwise expand the inner lumen of the artery. The balloon is then deflated so that blood flow can be resumed through the dilated artery and the dilatation catheter can be removed therefrom. Further details of dilatation catheters, guidewires, and devices associated therewith for angioplasty procedures can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson, et al.); U.S. Pat. No. 4,554,929 (Samson, et al.); U.S. Pat. No. 4,616,652 (Simpson); U.S. Pat. No. 4,638,805 (Powell); U.S. Pat. No. 4,748,982 (Horzewski, et al.); U.S. Pat. No. 5,507,768 (Lau, et al.); U.S. Pat. No. 5,451,233 (Yock); and U.S. Pat. No. 5,458,651 (Klemm, et al.), which are hereby incorporated herein in their entirety by reference thereto.

One problem which can occur during balloon angioplasty procedures is the formation of intimal flaps which can collapse and occlude the artery when the balloon is deflated at the end of the angioplasty procedure. Another problem characteristic of balloon angioplasty procedures is the large number of patients which are subject to restenosis in the treated artery. In the case of restenosis, the treated artery may again be subjected to balloon angioplasty or to other treatments such as by-pass surgery, if additional balloon angioplasty procedures are not warranted. However, in the event of a partial or total occlusion of a coronary artery by the collapse of a dissected arterial lining after the balloon is deflated, the patient may require immediate medical attention, particularly in the coronary arteries.

A focus of recent development work in the treatment of heart disease has been directed to endoprosthetic devices called stents. Stents are generally cylindrically shaped intravascular devices which are placed within an artery to hold it open. The device can be used to prevent restenosis and to maintain the patency of a blood vessel immediately after intravascular treatments. In some circumstances, they can also be used as the primary treatment device where they are expanded to dilate a stenosis and then left in place.

One method and system developed for delivering stents to desired locations within the patient's body lumen involves crimping a stent about an expandable member, such as a balloon on the distal end of a catheter, advancing the catheter through the patient's vascular system until the stent is in the desired location within a blood vessel, and then inflating the expandable member on the catheter to expand the stent within the blood vessel. The expandable member is then deflated and the catheter withdrawn, leaving the expanded stent within the blood vessel, holding open the passageway thereof.

However, retaining the position of the stent in the proper location on the expandable member while advancing the catheter through the body lumen has been found to be difficult. If the stent is dislodged from or moved on the expandable member the system will not correctly deliver the stent into the body lumen. This would require repeating the procedure. This delays insertion of the stent into the body lumen and lengthens the time of the stenting procedure.

Different methods have been attempted to maintain the position of the stent on the expandable member. One such method involves a protective sheath surrounding the catheter and stent assembly, which is retracted prior to inflation of the expandable member. The use of the sheath, however, increases the profile of the catheter assembly which must traverse narrow vessels and the sheath reduces the flexibility of the distal end of the delivery catheter. It would be an improvement to use a technique which does not increase the overall profile of the catheter assembly and maintains the flexibility of the delivery catheter.

Another method has been to remove the friction reducing coating on the expandable member in the location of the stent thereby allowing the catheter assembly's pre-coated surface to hold the stent in frictional contact. This method has not proven highly efficient in maintaining the stent in the desired location.

What has been needed and heretofore unavailable is a highly efficient means of maintaining a stent in a desired location on a stent delivery system without increasing the overall profile of the catheter assembly or compromising the flexibility. The present invention satisfies this need.

SUMMARY OF THE INVENTION

This invention is directed to an improvement in stent delivery systems for removably securing a stent onto an expandable member. Securing the stent is accomplished by tightly crimping the stent onto the balloon portion of a catheter wherein a deformable material has been disposed. By compressing the deformable material the stent is secured due to the increased frictional contact and interference between the stent and the compressed catheter assembly.

Stent delivery systems are typically composed of an elongated tubular member, or catheter, encompassed by an expandable member such as an inflatable balloon. The stent is located about the expandable member so that the two can be expanded together. The improvement of this invention includes introducing a deformable material into the space between the tube member and the expandable member. The deformable material may be adhered to the elongated tube member, the expandable member, or injected into the space therebetween. The stent is then crimped onto the expandable member so that the deformable material is compressed. The deformable material may be compressed with sufficient force to form pockets of material within the deformable material corresponding to gaps within the structure of the stent. The deformable material may also extend beyond one or both of the longitudinal ends of the stent so that sufficient crimping force can be applied on the expandable stent to form ridges in the deformable material located beyond the ends of the stent.

This invention can be used with the known configurations of stent delivery catheter assemblies including over-the-wire (OTW) intravascular catheters and rapid exchange (Rx) intravascular catheters.

The deformable material may be composed of elastomeric or silastic material. The deformable material may also contain a viscid surface to aid in holding down the expandable member and avoid bunching. Furthermore the deformable material may be cured into shape after being compressed.

The present invention results in a simplified method of inserting the stent into the body lumen. The catheter assembly is inserted into the body lumen without further steps being taken to secure the stent. The expandable member is inflated at the desired location expanding and implanting the stent within the body lumen. When the expandable member is then deflated, the stent is released and the remainder of the catheter assembly may be withdrawn leaving the stent implanted within the body lumen.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is a partial cross-sectional view depicting a stent delivery system depicting elements of the invention prior to crimping.

FIG. 2 is a cross-sectional view taken along lines 2—2 in FIG. 1.

FIG. 3 is a cross-sectional view taken along line 3—3 in FIG. 1.

FIG. 4 is a cross-sectional view taken along line 4—4 in FIG. 1.

FIG. 7 is a partial cross-sectional view depicting a stent delivery system configured as a rapid exchange catheter incorporating the invention.

FIG. 8 is a cross-sectional view taken along lines 8—8 in FIG. 7.

FIG. 9 is a cross-sectional view taken along lines 9—9 in FIG. 7.

FIG. 10 is a cross-sectional view taken along the lines 10—10 shown in FIG. 7.

FIG. 13 depicts a longitudinal cross-sectional view of a body lumen and an elevational view of a stent delivery system where the stent has been expanded.

FIG. 14 is a cross-sectional view taken along lines 14—14 in FIG. 13.

FIG. 15 is a cross-sectional view depicting a partially withdrawn stent delivery system.

DETAILED DESCRIPTION OF PREFERRED EMBODIMENTS

Figure 5:
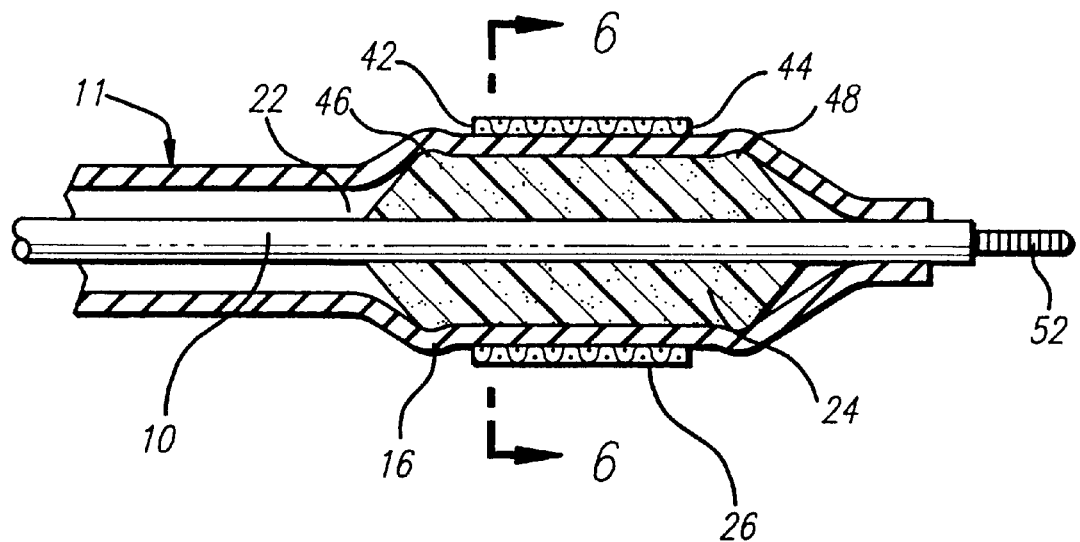
FIG. 5 is a cross-sectional view of the corresponding area in FIG. 1 after crimping the stent onto the expandable member of the catheter.

FIGS. 1 through 6 illustrate a catheter assembly with a removably secured stent which embodies the features of the invention. Generally, catheter assembly 8 includes inner tubular member 10 and outer tubular member 11 aligned about the inner tubular member. The outer tubular member has expandable member 16 incorporated within the member, located adjacent the distal end of the inner tubular member. The inner tubular member and the expandable member define annular space 22 between them. A deformable material 24 is located in annular space 22, preferably connected to outer surface 12 of inner tubular member 10. An expandable stent 26 is positioned around expandable member 16. When stent 26 is tightly crimped about outer surface 20 of expandable member 16, inner surface 18 of the expandable member will compress deformable material 24. This configuration secures expandable stent 26 in the proper location while the stent is inserted into a body lumen by increasing the frictional contact between the expandable stent and outer surface 20 of the expandable member due to the compression of deformable material 24. This configuration presents an improvement to stent delivery systems by increasing the efficiency of delivering and implanting the stent in the body lumen.

Stent delivery systems are typically composed of inner tubular member and outer tubular member 11 with inflatable means, such as expandable members, attached to the distal end. The expandable member 16 preferably is attached to or is one piece and formed from the outer member, and is aligned about the inner tubular member, thereby defining an annular space 22 between the two. This allows inflation fluid to inflate the expandable member. Crimping expandable stent 26 about the expandable member allows the two to be expanded together. The improvement of this invention is to removably retain the stent onto the expandable member by applying deformable material within the annular space.

Expandable stents 26 are generally composed of a lattice configuration which defines gaps 28 within the stent's body. In one embodiment of the invention, expandable stent 26 is crimped about expandable member 16 and deformable material 24 with sufficient force to cause pockets of material 30 to form in the deformable material and which correspond with gaps 28 in the stent. This pocketing further enhances the retention of the expandable stent by increasing the interference between the stent and the combination of the expandable member and the deformable material. This configuration is most clearly illustrated at FIG. 6.

Another embodiment of the invention is to extend deformable material 24 within the annular space beyond the location where one or both of longitudinal ends 42,44 of expandable stent 26 will be located on outer surface 20 of expandable member 16. The expandable stent is then crimped about the expandable member and the deformable material with sufficient force to cause ridges 46,48 to be formed beyond one or both ends of the stent. These ridges 46,48 further enhance the retention of the expandable stent by increasing the interference between the stent and the combination of the expandable member and the deformable material. Another advantage of this embodiment is in increasing the diameter of the expandable member distal to the stent. The increased diameter just distal to the stent helps to hold the stent on the expandable member as the delivery catheter is advanced through sometimes tortuous body lumens.

This stent delivery catheter assembly can be configured by modifying commonly known stent delivery systems. On many of these systems, the expandable member 16 is an inflatable balloon. FIGS. I through 6 show the catheter assembly configured as an over-the-wire (OTW) intravascular catheter 34. FIGS. 7 through 10 and FIGS. 11 through 15 show the catheter assembly configured as a rapid exchange (Rx) intravascular catheter 36. The Rx configuration typically requires fluid inflation lumen 40 to be positioned within inner tubular member 10, which allows inflation fluid access into annular space 22, through port 60 for inflation of expandable member 16.

Deformable material 24 may be attached to outer surface 12 of inner tubular member 10 as shown in the figures. Another embodiment, not shown in the figures, is to inject the deformable material into annular space 22 without attaching it to any surface. Another embodiment, not shown in the figures, is to attach the deformable material onto inner surface 18 of expandable member 16. When the catheter assembly is configured as an Rx intravascular catheter 36 and the deformable material is attached to outer surface 12 of inner tubular member 10, the deformable material is configured so as not to obscure port 60 or the fluid communication between annular space 22 and fluid inflation lumen 40 of inner tubular member 10.

Deformable material 24 may be formed from generally available materials including elastomeric and silastic materials. In a preferred embodiment, an elastomeric material commercially available as C-Flex is used, which is a trademark of Consolidated Polymer Technologies Corporation. This material can be preformed into a thin-walled cylinder (about 0.005 inch wall thickness) and then heat shrunk over inner tubular member 10. This cylinder can be trimmed to the same length or slightly longer than the stent length (approximately 20 mm for a 20 mm stent). Polyurethane is another possible material which has a viscid surface. Silastic, or silicon rubber materials have the advantage of being sufficiently deformable to flow into the annular space to form the deformable material.

The invention may also use a deformable material 24 which is cured after the stent has been crimped onto the catheter assembly. Several materials may be used as curable deformable materials. Depending on what material is used, the curable deformable material preferably may be cured using, for example, heat cures, time cures or ultraviolet cures. Another embodiment uses the adhesive commercially available as LOCTITE 33-11, a trademark of the Lotite Corporation. This material uses an ultraviolet cure. Using a curable material has the advantage that the deformable material maintains its shape after curing and during stent delivery.

FIGS. 1 through 6 further illustrate a method for configuring a catheter assembly with a removably secured expandable stent 26. FIG. 3 shows inner tubular member 10 having expandable member 20 aligned about it, thereby defining an annular space 22 therebetween. The first step in the method is providing deformable material 24 within annular space 22. A preferred method involves attaching the deformable material to outer surface 12 of inner tubular member 10. Furthermore, a preferred method involves extending the deformable material beyond the location where one or both ends 42,44 of expandable stent 26, will be mounted.

Figure 6:
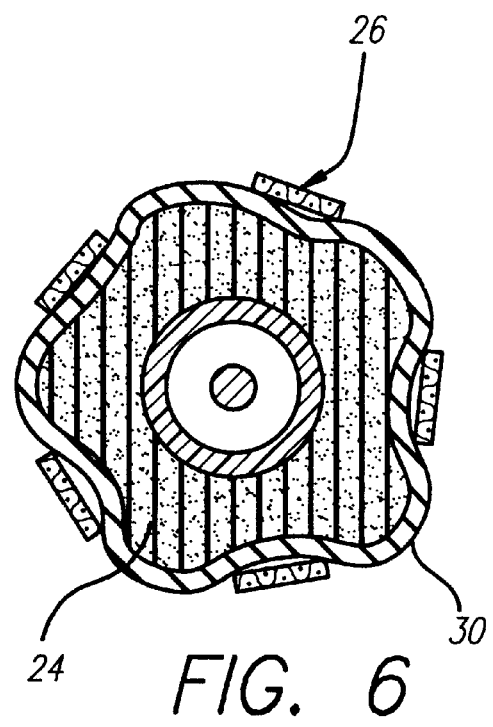
FIG. 6 is a cross-sectional view taken along lines 6—6 in FIG. 5.
Figure 11:
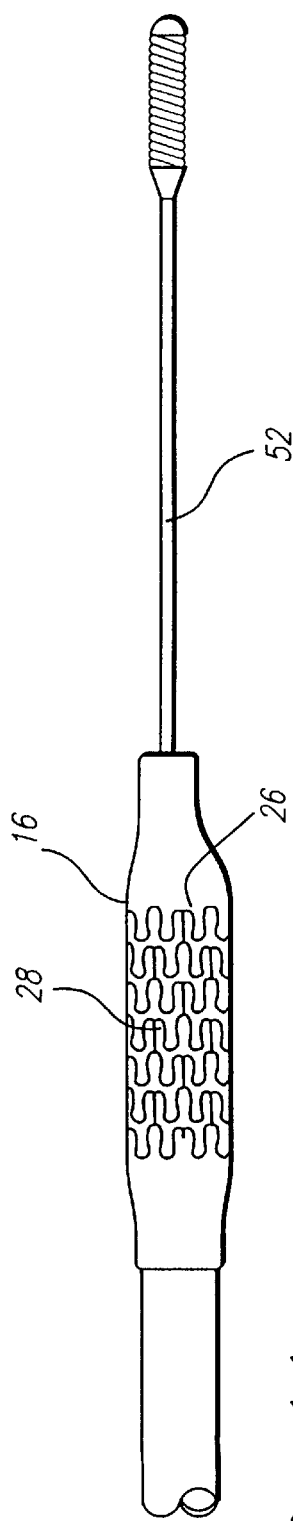
FIG. 11 is a plan view of a stent delivery system having a rapid exchange configuration and including elements of the invention.
Figure 12:
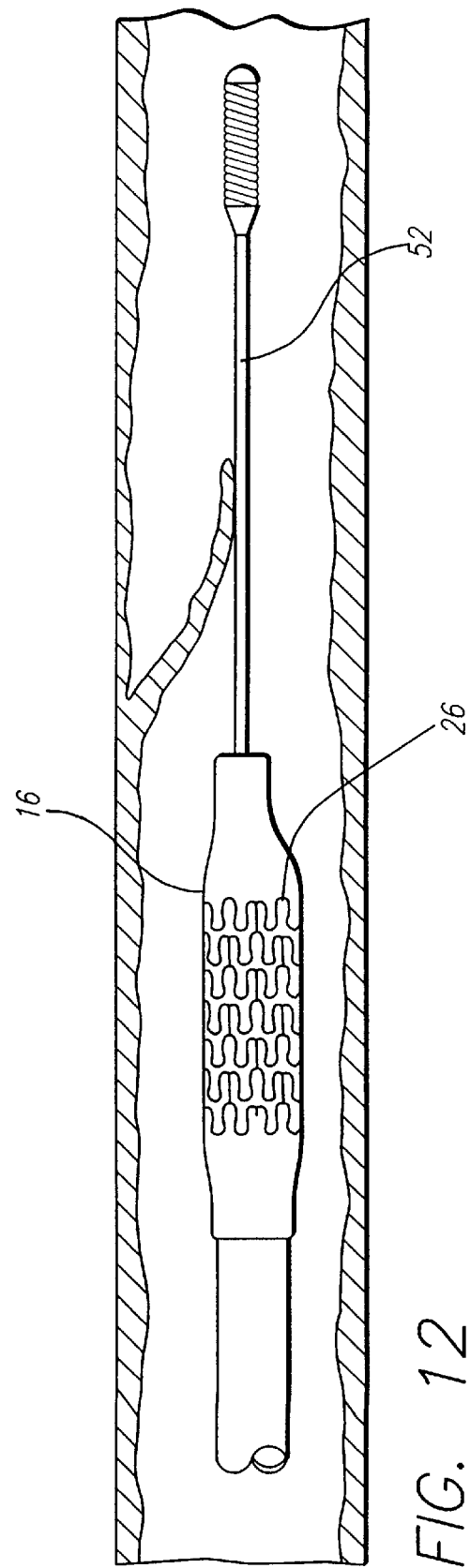
FIG. 12 is a longitudinal cross-sectional view of a body lumen depicting an elevational view of a partially inserted stent delivery system.

The next step is to crimp the expandable stent onto outer surface 20 of expandable member 16 so that inner surface 18 of expandable member 16 compresses deformable material 24. FIGS. 5 and 6 most clearly illustrate the results of this step. A preferred method includes crimping the expandable stent with sufficient force to produce pockets of material 30 in deformable material 24 corresponding to gaps 28 in the stent. Furthermore, it is preferable to crimp the expandable stent with sufficient force to produce ridges 46,48 in the deformable material which extends beyond one or both ends of the stent.

When using a curable material, the additional step of curing deformable material 24 is required after crimping the expandable stent 26 and compressing the deformable material. Curing the deformable material may comprise an ultraviolet, heat or time cure, which is commonly known. The method used is dependent on the deformable material chosen and known to persons of ordinary skill in the art. This step results in the deformable material maintaining its shape after being compressed.

The present invention catheter assembly with a removably secured stent can be used for delivering and implanting a stent into a body lumen when used in combination with stent delivery systems. These systems include modified over-the-wire (OTW) catheters 34 and rapid exchange (Rx) catheters 36. FIGS. 11 through 15 illustrate an exemplary use of the invention using an Rx catheter. The catheter assembly 36 with expandable stent 26 crimped firmly in place on expandable member 16 is inserted into a body lumen, e.g., a coronary artery. FIGS. 12 through 15 illustrate a typical situation in which the invention is used after an intravascular procedure has damaged a patient's arterial lining to such an extent that the lining needs support to prevent it from collapsing into the arterial passageway and obstructing blood flow through the artery. In these situations, as others, the stent can be delivered to, and implanted into, the location requiring support without the use of further means to secure the stent.

Catheter assembly 36 is advanced along guide wire 52, which is already in position distal to the location requiring support. As illustrated in FIG. 13, expandable member 16 is inflated thereby expanding stent 26. This may be accomplished, for example, by injecting fluid into annular space 22 under substantial pressure (4 to 10 atm is preferred). Expandable member 16 is then deflated leaving expandable stent 26 expanded and implanted in the desired location of the body lumen. The remainder of the catheter assembly, with the expandable member deflated and no longer in frictional contact with the expandable stent, is then withdrawn from the body lumen.

The dimensions of the intravascular catheter will generally follow the dimensions of intravascular catheters used in angioplasty procedures in the same arterial location. Typically, the length of a catheter for use in the coronary arteries is about 150 cm, the outer diameter of the catheter shaft is about 0.035 inch (0.89 mm), the length of the balloon is typically about 20 mm and the inflated diameter about 1 to about 8 mm.

The materials of construction for the inner tubular member and expandable member may be selected from those used in conventional balloon angioplasty catheters, such as those described in the patents incorporated by reference.

While the present invention has been described herein in terms of delivering an expandable stent to a desired location within a patient's blood vessel, the delivery system can be employed to deliver stents to locations within other body lumens so that the stents can be expanded to maintain the patency of those body lumens. This invention may also be used to deliver and implant other intravascular prosthesis, such as tube grafts to treat abdominal aortic aneurisms. Various changes and improvements may also be made to the invention without departing from the scope thereof.

What is claimed is:

1. A catheter assembly for removably securing an expandable stent during stent delivery and implanting within a body lumen, comprising:

the catheter assembly having an outer tubular member and an inner tubular member, the outer tubular member having a proximal end and a distal end;

the inner tubular member having a proximal end and a distal end and having an outer surface and including at least one inner lumen;

an expandable member associated with the outer tubular member and adjacent to the outer tubular member distal end, the expandable member having an inner surface and an outer surface with the inner surface of the expandable member and the outer surface of the inner tubular member defining an annular space therebetween;

a deformable material located within the annular space and extending for some length;

an expandable stent tightly crimped onto the outer surface of the expandable member thereby compressing the expandable member and deforming the deformable material, wherein the expandable stent is sized and positioned such that the deformable material extends substantially the length of the stent when the stent is mounted onto the expandable member, and wherein the expandable stent comprises a configuration defining gaps in the stent; and pockets of material formed in the deformable material, said pockets corresponding to the gaps in the stent.

2. The catheter assembly of claim 1, wherein the expandable stent comprises a lattice configuration.

3. The catheter assembly of claim 1, wherein the pockets correspond to less than all of the gaps in the stent.

4. The catheter assembly of claim 1, wherein the expandable stent includes a distal end and a proximal end and the deformable material extends proximal to at least the proximal end forming a ridge in the deformable material proximal to the proximal end of the stent as a result of the stent being crimped on the expandable member thereby compressing the deformable material.

5. The catheter assembly of claim 1, wherein the expandable stent includes a distal end and a proximal end, the deformable material extending distal of at least the distal end forming a ridge in the deformable material distal to the distal end of the stent as a result of the stent being crimped on the expandable member thereby compressing the deformable material.

6. The catheter assembly of claim 1, wherein the expandable stent includes a distal end and a proximal end and the deformable material extends beyond the ends forming a first ridge in the deformable material distal to the distal end of the stent, and a second ridge in the deformable material proximal to the proximal end of the stent as a result of the stent being crimped on the expandable member thereby compressing the deformable material.

7. The catheter assembly of claim 1, wherein the expandable member is an inflatable balloon.

8. The catheter assembly of claim 1, further comprising means for delivering the stent through a body lumen.

9. The catheter assembly of claim 8, wherein the delivery means includes an over-the-wire intravascular catheter.

10. The catheter assembly of claim 8, wherein the delivery means includes a rapid exchange intravascular catheter.

11. The catheter assembly of claim 8, wherein the inner tubular member also includes a fluid inflation lumen having a port in fluid communication with the annular space.

12. The catheter assembly of claim 1, wherein the deformable material is attached to the outer surface of the inner tubular member within the annular space.

13. The catheter assembly of claim 11, wherein the deformable material is attached to the outer surface of the inner tubular member within the annular space, so that the port and the fluid inflation lumen are not obstructed.

14. The catheter assembly of claim 1, wherein the deformable material is formed from an elastomeric material.

15. The catheter assembly of claim 1, wherein the deformable material is formed from a silastic material.

16. A catheter assembly for removably securing an expandable stent during stent delivery and implanting within a body lumen, comprising:

the catheter assembly having an outer tubular member and an inner tubular member, the outer tubular member having a proximal end and a distal end;

the inner tubular member having a proximal end and a distal end and having an outer surface and including at least one inner lumen;

an expandable member associated with the outer tubular member and adjacent to the outer tubular member distal end, the expandable member having an inner surface and an outer surface with the inner surface of the expandable member and the outer surface of the inner tubular member defining an annular space therebetween; and a deformable material located within the annular space and extending for some length, wherein the deformable material is attached to the inner surface of the expandable member within the annular space, and an expandable stent tightly crimped onto the outer surface of the expandable member thereby compressing the expandable member and the deformable material.

17. The catheter assembly of claim 16, wherein the deformable material has a viscid surface for holding the expandable member when the expandable member is compressed onto the viscid surface.

18. A method for removably securing an expandable stent on a catheter assembly, the method comprising:

providing an assembly comprising;
an outer tubular member having a proximal end and a distal end, an inner tubular member having a proximal end and a distal end and having an outer surface, an expandable member associated with the outer tubular member and adjacent to the outer tubular member distal end, the expandable member having an inner surface and outer surface wherein the inner surface of the expandable member and the outer surface of the inner tubular member define an annular space therebetween, and an expandable stent for mounting onto the expandable member;

providing a deformable material within the annular space; and crimping the expandable stent onto the expandable member with sufficient force to compress the expandable member and to deform the deformable material.

19. The method of claim 18, wherein providing the deformable material into the annular space includes attaching the deformable material to the outer surface of the inner tubular member.

20. A method for removably securing an expandable stent on a catheter assembly, the method comprising:

providing an assembly comprising;
an outer tubular member having a proximal end and a distal end, an inner tubular member having a proximal end and a distal end and having an outer surface, an expandable member associated with the outer tubular member and adjacent to the outer tubular member distal end, the expandable member having an inner surface and outer surface wherein the inner surface of the expandable member and the outer surface of the inner tubular member define an annular space therebetween, and an expandable stent for mounting onto the expandable member;
providing a deformable material within the annular space, including attaching the deformable material to the inner surface of the expandable member; and
crimping the expandable stent onto the expandable member thereby compressing the expandable member and the deformable material.

21. The method of claim 18, wherein the expandable stent provided is formed of a lattice configuration defining gaps in the stent, and the step of crimping the stent onto the expandable member includes crimping with sufficient force to compress the deformable material and form pockets in the deformable material corresponding to the gaps in the stent.

22. The method of claim 18, wherein the expandable stent includes a distal end and a proximal end, the deformable material extending distal of the distal end, and the step of crimping the stent onto the expandable member includes crimping with sufficient force to form a ridge in the deformable material that extends distal to the distal end.

23. The method of claim 18, wherein the expandable stent includes a distal end and a proximal end and the deformable material extends proximal to the proximal end, and the step of crimping the stent onto the expandable member includes crimping with sufficient force to form a ridge in the deformable material that extends proximal to the proximal end.

24. The method of claim 18, wherein the expandable stent includes a distal end and a proximal end and the expandable material extends beyond the distal end and the proximal end, and the step of crimping the deformable stent onto the expandable member includes crimping with sufficient force to form a first ridge distal to the distal end and a second ridge proximal to the proximal end.

25. A catheter assembly for removably securing an expandable stent during stent delivery and implanting within a body lumen, comprising:

the catheter assembly having an outer tubular member and an inner tubular member, the outer tubular member having a proximal end and a distal end;
the inner tubular member having a proximal end and a distal end and having an outer surface and including at least one inner lumen;
an expandable member associated with the outer tubular member and adjacent to the outer tubular member distal end, the expandable member having an inner surface and an outer surface with the inner surface of the expandable member and the outer surface of the inner tubular member defining an annular space therebetween;
a deformable material located within the annular space and extending for some length; and
an expandable stent tightly crimped onto the outer surface of the expandable member, wherein the stent includes a first end and a second end, wherein the deformable material extends underneath the stent and beyond at least the first end of the stent, the deformable material forming a first ridge in the deformable material beyond the first end of the stent as a result of the stent being crimped on the expandable member thereby compressing the deformable material.

26. The catheter assembly of claim 25, wherein the first end of the stent is a distal end, and the second end of the stent is a proximal end, wherein the deformable material extends beyond the ends forming the first ridge in the deformable material distal to the distal end of the stent, and a second ridge in the deformable material proximal to the proximal end of the stent as a result of the stent being crimped on the expandable member thereby compressing the deformable material.

27. A method for removably securing an expandable stent on a catheter assembly, the method comprising:

providing an assembly comprising;
an outer tubular member having a proximal end and a distal end, an inner tubular member having a proximal end and a distal end and having an outer surface, an expandable member associated with the outer tubular member and adjacent to the outer tubular member distal end, the expandable member having an inner surface and outer surface wherein the inner surface of the expandable member and the outer surface of the inner tubular member define an annular space therebetween, and an expandable stent for mounting onto the expandable member;
providing a deformable material within the annular space;
crimping the expandable stent onto the expandable member thereby compressing the expandable member and the deformable material; and
curing the deformable material after crimping the expandable stent onto the expandable member.

28. The method of claim 18, wherein providing the deformable material the annular space includes, forming a cylinder of elastomeric material, placing the cylinder around the outer surface of the inner tubular member, and heat-shrinking the cylinder onto the inner member.

29. A method of delivering and implanting a removably secured expandable stent to a desired location within a body lumen, the method comprising:

providing a catheter assembly comprising an outer tubular member having a distal end and a proximal end and an inner tubular member having a distal end and a proximal end and having an outer surface, and at least one internal lumen extending within the inner tubular member; an expandable member aligned about the inner tubular member and attached adjacent to the outer tubular member distal end, the expandable member having an inner surface and an outer surface wherein the inner surface of the expandable member and the outer surface of the inner tubular member define an annular space therebetween; a deformable material disposed within the annular space; and an expandable stent tightly crimped onto the expandable member with sufficient force to deform the deformable material so that frictional contact between the expandable stent and the expandable member is enhanced by the resultant contact between the expandable member and the deformable material thereby removably retaining the expandable stent in place during delivery of the stent through the body lumen;

advancing the catheter assembly through the body lumen to the desired location;

inflating the expandable member thereby expanding and implanting the stent at the desired location;

deflating the expandable member so that the expandable stent is no longer in contact with the catheter assembly;

withdrawing the catheter assembly from the body lumen.

* * * * *

UNITED STATES PATENT AND TRADEMARK OFFICE
CERTIFICATE OF CORRECTION

PATENT NO.   : 6,193,727 B1
DATED        : February 27, 2001
INVENTOR(S)  : Philip C. Foreman, et al.

Page 1 of 1

It is certified that error appears in the above-identified patent and that said Letters Patent is hereby corrected as shown below:

<u>Title page,</u>
Under "U.S. PATENT DOCUMENTS", add the following:
-- 5,108,416    4/1992      Ryan, et al.
   5,158,548    10/1992     Lau, et al.
   5,242,399    9/1993      Lau, et al.
   5,344,426    9/1994      Lau, et al.
   5,445,646    8/1995      Euteneuer, et al.
   5,514,154    5/1996      Lau, et al.
   5,571,135    11/1996     Fraser, et al.
   5,759,474    2/1998      Rupp, et al.
   5,836,965    11/1998     Jendersee, et al. --.

After "5,893,852 * 1/1999 Morales", add
-- FOREIGN PATENT DOCUMENTS
   98/07390    2/1998  (WO)
   0 974 315   1/2000  (EP) --.

<u>Claim 19, column 9,</u>
Line 5, change "into", to read -- in --.

<u>Claim 28, column 10,</u>
Line 45, after "material", add -- in --.

Signed and Sealed this

Thirtieth Day of October, 2001

Attest:

NICHOLAS P. GODICI
*Attesting Officer*   *Acting Director of the United States Patent and Trademark Office*